(12) United States Patent
Quintana et al.

(10) Patent No.: US 7,447,335 B1
(45) Date of Patent: Nov. 4, 2008

(54) APPARATUS FOR DETECTION OF OBJECTS

(75) Inventors: Alvin L. Quintana, Ridgecrest, CA (US); Daniel Garcia, Inyokern, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/874,520

(22) Filed: Oct. 18, 2007

Related U.S. Application Data

(63) Continuation of application No. 10/956,703, filed on Sep. 29, 2004, now abandoned.

(51) Int. Cl.
  *G06K 9/00* (2006.01)
  *G01N 21/00* (2006.01)
  *G03B 17/00* (2006.01)

(52) U.S. Cl. .................. 382/103; 359/808; 356/241.1; 348/169

(58) Field of Classification Search .................. 382/103
  See application file for complete search history.

(56) References Cited

U.S. PATENT DOCUMENTS

| | | | | |
|---|---|---|---|---|
| 5,822,137 A | * | 10/1998 | Abul-Haj et al. | 359/808 |
| 6,370,260 B1 | * | 4/2002 | Pavlidis et al. | 382/103 |
| 6,538,732 B1 | * | 3/2003 | Drost et al. | 356/241.1 |

* cited by examiner

*Primary Examiner*—Samir A Ahmed
*Assistant Examiner*—John W Lee
(74) *Attorney, Agent, or Firm*—Brian F. Drazich

(57) ABSTRACT

The present invention relates to an apparatus for locating objects (such as exploded or unexploded ordnance). The embodiments take advantage of spectroscopic features of an object's paint or surface finish to discriminate between the object and the background area. The apparatus utilizes an optical sensor, filters and the application of pixel to pixel ratios to detect the paint on an object from a distance so that objects such as unexploded ordnance may be safely destroyed or neutralized.

14 Claims, 3 Drawing Sheets

APPARATUS FOR DETECTION OF OBJECTS

CROSS-REFERENCE TO RELATED APPLICATIONS

This application is a continuation of U.S. patent application Ser. No. 10/956,703, filed Sep. 29, 2004, now abandoned, which was concurrently filed with U.S. patent application Ser. No. 10/956,702, pending.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The present invention relates generally to an apparatus for detecting objects and more particularly utilizing optical means for locating ordnance on the ground.

BACKGROUND OF THE INVENTION

The elimination of unexploded ordnance (UXO) on land presents a serious problem for both military and civilian personnel. Current technology provides many passive and active systems for the detection of subterranean unexploded ordnance, such as mines. Unexploded ordnance may also lay on the surface but be partially obscured (such as by foliage) or partially buried. Often large numbers of unexploded ordnance must be located over an area (such as a practice range). Unexploded ordnance addresses many issues including safety and environmental issues such as pollution prevention.

The basic operation of removing or disposing of the unexploded ordnance includes detecting them, assessing their condition and disposing of them. Unless the UXO is obviously in safe condition the common method of disposal is to destroy or disarm them in their present location. The task of detecting UXO is painstaking and dangerous, requiring a thorough canvassing of the area. There exists a need to detect and locate UXO safely and economically.

SUMMARY OF THE INVENTION

An embodiment of the present invention includes an apparatus for detecting at least one object such as for example, unexploded ordnance including an optical sensor taking a first image of a scene containing an object having a paint on its exterior utilizing a first bandpass filter centered on a lower boundary wavelength of a transition area on a plot of diffuse reflectance of a sample of the paint. The embodiment further includes the optical sensor taking a second image of the scene utilizing a second bandpass filter centered on an upper boundary wavelength of the transition area. A third image of the scene is derived from a pixel by pixel ratio of the second image to the first image, with the third image revealing areas of the paint, thereby detecting the object.

It is to be understood that the foregoing general description and the following detailed description are exemplary only and are not to be viewed as being restrictive of the present invention as claimed. These and other objects, features and advantages of the present invention will become apparent after a review of the following detailed description of the disclosed embodiments and the appended claims.

DETAILED DESCRIPTION OF THE INVENTION

Figure 1:
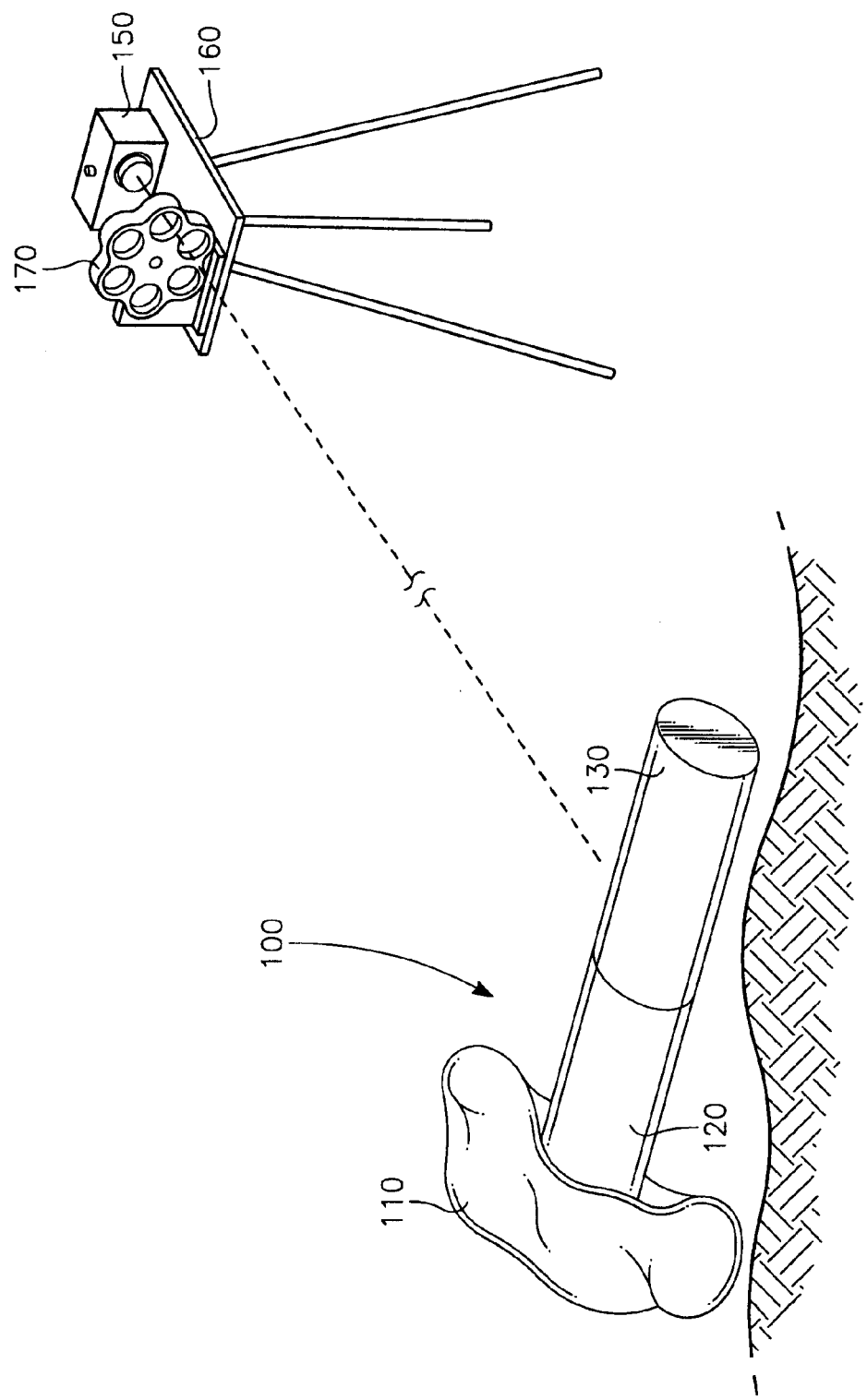
FIG. 1 illustrates the detection of a BLU-97 submunition according to an embodiment of the present invention.

Embodiments of the present invention include an apparatus and a method for locating ordnance (exploded or unexploded) that lay on the surface and may be partially obscured. The embodiments of the present invention take advantage of spectroscopic features of an ordnance's paint or surface finish to discriminate between the ordnance and the background area. The apparatus is an optical detection system including an optical sensor and filters and the application of pixel to pixel ratios to detect the paint on an ordnance from a distance so that the ordnance may be safely destroyed or neutralized. It should be understood that the examples and embodiments described herein are for illustrative purposes only and that various modifications or changes in light thereof will be suggested to persons skilled in the art and are to be included within the spirit and purview of this application and the scope of the appended claims. For example, embodiments of the present invention may be applied to detecting many objects and is not limited to the detection of ordnance.

Characteristics of Ordnance Paint

Samples of area soil typical of an expected background and of ordnance exterior paint are taken. The samples' diffuse reflectance over a broad span of wavelengths is measured using a spectrophotometer with diffuse reflectance measurement capability. Plots are created of the samples diffuse reflectance as a function of wavelength. The diffuse reflectance curves are examined for distinct characteristics and differences. For example, the diffuse reflectance curves for soil samples show a relatively well behaved (nearly linear) decrease of reflectance as wavelength decreases (see FIG. 2). However the diffuse reflectance curves of paint samples have a significant change of reflectivity within a narrow area band of wavelength (a transition area). A significant change in reflectivity is any change that is detectable against a given background and with a sensor that has certain noise and dynamic range characteristics. For example the minimum detectable change in reflectivity across a 50 nanometer band in the blue-green, with a sandy background and with an 8 bit camera is around a factor of 1.5. The transition area has a lower and upper boundary wavelength. The boundary wavelengths are chosen so as to provide the best contrast between the soil samples and the paint samples across the transition area. The diffuse reflectance curves are normalized to the wavelength of the lower boundary.

In another embodiment of the present invention, the determination of the characteristics may be automated. Once the reflectivity vs. wavelength data is taken on the paint and background samples an algorithm can be run to detect a slope change in the paint reflectivity and compare the change in reflectivity before and after the slope to the change in reflectivity of the background sample across the same span of wavelengths. If the ratio of reflectivity crosses a predetermined threshold and provides a predetermined contrast to the background then a spectral feature has been identified.

Detect Ordnance

In an embodiment of the present invention the scene is imaged with an optical sensor utilizing bandpass filters centered about the upper and lower boundary wavelengths of the transition area (previously determined as described above) without moving between exposures. A pixel by pixel ratio is taken between these two images (the ratio of the upper wavelength image to the lower wavelength image) to derive a third image based on the different reflectivities of the objects in the scene, thereby detecting areas of ordnance paint. To differentiate between the ordnance and other "clutter", a threshold is applied to eliminate pixels that do not display the correct ratio of reflectivities for the desired paint. The threshold value is chosen and applied so as to better discriminate between the desired objects (ordnance) and other objects when they are very close in color. One embodiment of the present invention includes imaging by video camera in real time with suspected ordnance objects highlighted for further investigation by disposal personnel. Another embodiment of the present invention includes utilizing a digital still camera to take images of an area for processing. With a high resolution camera, relatively small areas of only a few pixels across of exposed ordnance may be detected in a large scene.

Embodiments of the present invention include conveying the location of the ordnance through relative image information as analyzed by means including the unaided or naked eye, as well as being marked or highlighted on a still or video image by automated means when an electronic optical sensor or the like is used. For example, an automated means includes using a computer to take the output of the detection algorithm and place a marker in the same location on the displayed image. The location information may be displayed on a map or in a 3 D image. The location information may take the form of a coordinate that is transferred to a higher level system that tracks of all possible detections for further investigation and destruction. Additional embodiments include an audible alarm when ordnance is located in the area being examined. Those of ordinary skill in the art will readily acknowledge that additional embodiments of the present invention according to the area of interest, the color of paint on different types of ordnance, the type of optical sensor, or other factors may be made without departing or diverting from the scope of the present invention.

AN EXAMPLE OF AN EMBODIMENT OF THE PRESENT INVENTION

FIG. 1 illustrates an example of ordnance detection according to an embodiment of the present invention. A field test was performed in an impact range area. The figure depicts a BLU-97 Class bomblet 100 as may be encountered in a practice range. The bomblet 100 includes a ballute 110, a fuze assembly 120, and the main charge section 130. The bomblets 100 may be scattered over a large area making it difficult for personnel to retrieve or neutralize them. The ballute 110 often becomes detached making it more difficult to detect the bomblet 100 with the human eye or any other apparatus or method.

Samples of range area soil and of BLU-97 paint were taken and the samples' diffuse reflectance over a broad range of wavelengths were measured using a spectrophotometer with diffuse reflectance measurement capability. BLU-97 bomblets were painted a yellow color on their exterior that has spectroscopic characteristics that vary rapidly across a narrow wavelength region between 500 and 550 nanometers (nm), even when the bomblets are aged by sun and weather (see FIG. 2).

A PixeLink™ PL-A641 camera 150 was mounted on a steady tripod 160. The camera includes a 9 degree FOV (field of view) with a 1.3 megapixel complementary metal oxide semiconductor (CMOS) sensor and a IEEE 1394 (firewire) output through which still frames are stored to a laptop computer. Each frame had a resolution of 1280×1024 pixels at 8 bits per pixel. The tripod also held a filter wheel 170 mounted so that the camera frames are taken through the filters mounted on the wheel 170.

Figure 2:
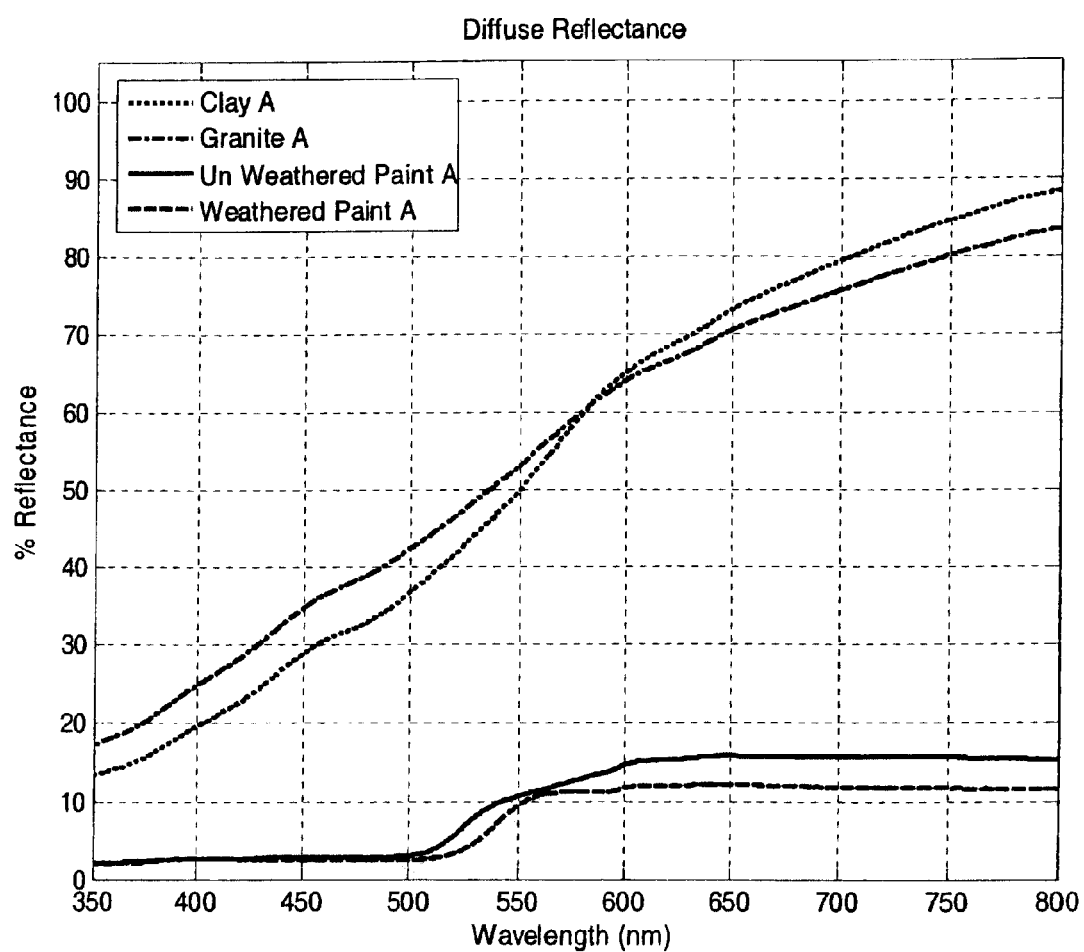
FIG. 2 is a plot of a sample's diffuse reflectance as a function of wavelength.

Two samples of paint were measured, one from a relatively unweathered sample and one from weathered debris found at an impact site. The weathered sample had been through an actual detonation. Two samples of soil were measured. The samples' diffuse reflectance over a broad span of wavelengths was measured using a spectrophotometer with diffuse reflectance measurement capability as discussed above. One sample tended to contain more granite sand content (designated granite) and one sample was designated clay because it contained some yellow coloration. FIG. 2 shows a plot of the samples' diffuse reflectance as a function of wavelength.

Figure 3:
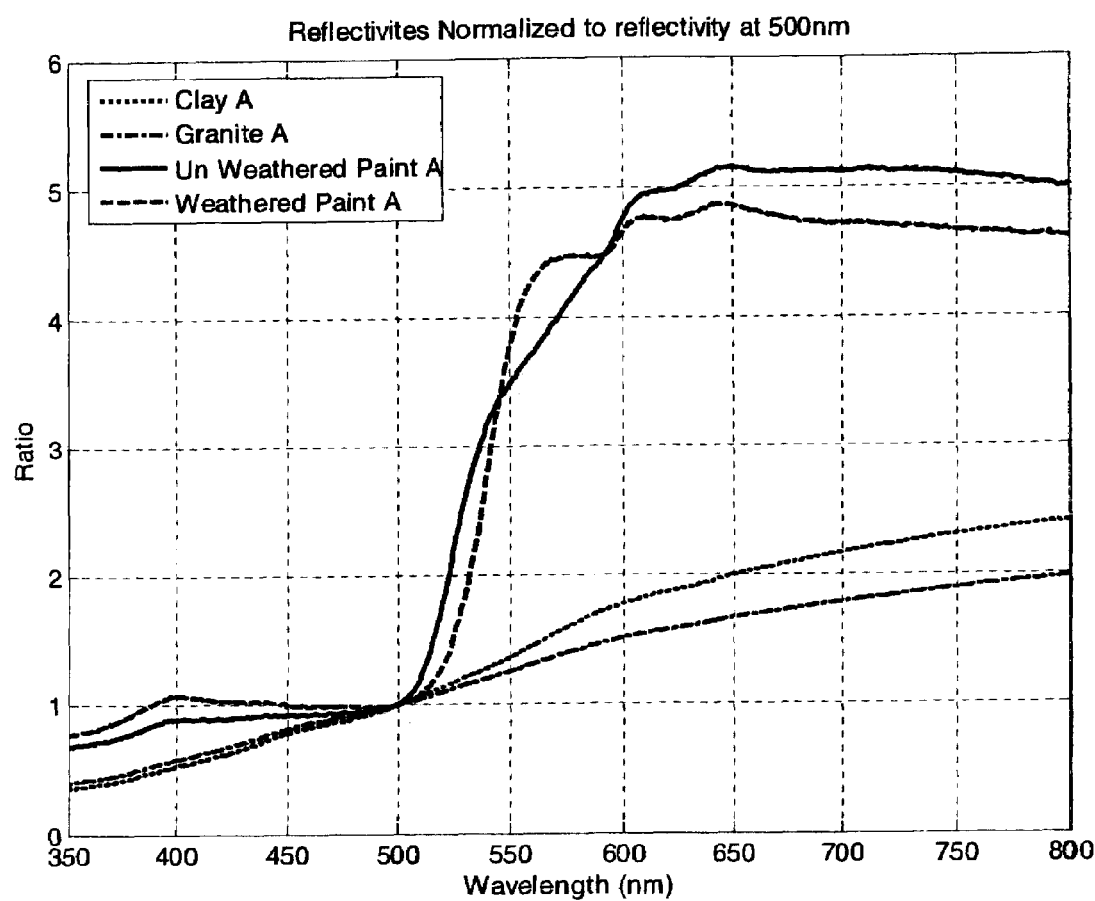
FIG. 3 is a plot of a sample's diffuse reflectance normalized to an inflection point.

FIG. 3 shows the reflectivities of the samples after each curve in FIG. 2 has been normalized to its own reflectance at 500 nm (the main inflection point of the paint). Using a 500 nm filtered image as a reference, FIG. 3 shows the expected ratios after pixel-to-pixel ratios are performed across images taken with filters of wavelengths other than 500 nm. The inflection point of 550 nm was selected because it offered the greatest ratio available with the least spread in wavelength (thereby minimizing the likelihood that a clutter object will have the same spectral ratio). This ties the detection process to objects that have this inflection characteristic (the ordnance paint). The filters mounted on the filter wheel 170 are centered at 500 and 550 nm and are each 10 nm full width at half maximum (FWHM).

Frames or scenes of the impact area were taken at various ranges to determine detection capability out to 500 feet. A BLU-97 shroud was placed in the FOV of the camera. The ordnance was detected in all scenes up to 500 feet. It is noteworthy that the threshold level was varied according to the location of the ordnance and was selected to differentiate between the ordnance yellow paint and other objects colored yellow (such as flowers in the impact range area).

Although the description above contains much specificity, this should not be construed as limiting the scope of the invention but as merely providing an illustration of the presently preferred embodiment of the invention. Thus the scope of this invention should be determined by the appended claims and their legal equivalents.

What is claimed is:

1. A method for detecting an object disposed on the surface of the earth comprising:
   selecting a site on the surface of the earth;
   providing a surface finish representative of an object to be detected;
   obtaining a diffuse reflectance spectrum of said surface finish;
   identifying a first inflection point of the largest increase in slope of the diffuse reflectance spectrum of said surface finish;
   associating a first wavelength region with said first inflection point;
   identifying a second inflection point of the largest decrease in slope of the diffuse reflectance spectrum of said surface finish;
   associating a second wavelength region with said second inflection point;
   choosing a specific area of said selected site for imaging;

passing light reflected from said specific area through a first bandpass filter that transmits light in said first wavelength region;

forming a first image of said specific area, comprised of light transmitted through said first bandpass filter, upon an optical sensor comprised of pixels;

passing light reflected from said specific area through a second bandpass filter that transmits light in said second wavelength region;

forming a second image of said specific area, comprised of light transmitted through said second bandpass filter, upon an optical sensor comprised of pixels such that each pixel of said second image is correlated with a pixel of said first image of said specific area;

calculating a ratio between each pair of correlated pixels of said first image and said second image;

defining a threshold magnitude;

calculating for each pair of said correlated pixels a value proportional to the difference between said threshold magnitude and the magnitude of said ratio;

assigning each said value to a pixel corresponding to each pair of said correlated pixels to form a third image of said specific area in which pixels on which surface finish reflectance is imaged have greater value than pixels on which surface soil reflectance is imaged.

2. A method for detecting an object disposed on the surface of the earth comprising:

selecting a site on the surface of the earth;

providing a surface finish representative of an object to be detected;

obtaining a diffuse reflectance spectrum of said surface finish;

identifying a first infection point of the largest increase in slope of the diffuse reflectance spectrum of said surface finish;

associating a first wavelength region with said first infection point;

identifying a second infection point of the largest decrease in slope of the diffuse reflectance spectrum of said surface finish;

associating a second wavelength region with said second infection point;

providing soil from the surface of the selected site;

obtaining a diffuse reflectance spectrum of said soil;

identifying the reflectance of said soil in said first wavelength region;

identifying the reflectance of said soil in said second wavelength region;

calculating a first ratio between said soil reflectance in said first wavelength region and in said second wavelength region;

defining a threshold magnitude based upon said first ratio between said soil reflectance in said first wavelength region and in said second wavelength region;

choosing a specific area of said selected site for imaging;

passing light reflected from said specific area through a first bandpass filter that transmits light in said first wavelength region;

forming a first image of said specific area, comprised of light transmitted through said first bandpass filter, upon an optical sensor comprised of pixels;

passing light reflected from said specific area through a second bandpass filter that transmits light in said second wavelength region;

forming a second image of said specific area, comprised of light transmitted through said second bandpass filter, upon an optical sensor comprised of pixels such that each pixel of said second image is correlated with a pixel of said first image of said specific area;

calculating a second ratio between each pair of correlated pixels of said first image and said second image;

calculating for each pair of said correlated pixels a value proportional to the difference between said threshold magnitude and the magnitude of said second ratio;

assigning each said value to a pixel corresponding to each pair of said correlated pixels to form a third image of said specific area in which pixels on which surface finish reflectance is imaged have greater value than pixels on which surface soil reflectance is imaged.

3. The method of claim 1 or claim 2 wherein said surface finish is paint.

4. The method of claim 1 or claim 2 wherein substantially simultaneously said first image is formed upon a first optical sensor and said second image is formed upon a second optical sensor.

5. The method of claim 1 or claim 2 wherein said first image and said second image are formed sequentially upon an optical sensor.

6. The method of claim 1 or claim 2 wherein the wavelengths within said first wavelength region are shorter than the wavelengths within said second wavelength region.

7. The method of claim 1 or claim 2 wherein the said first wavelength region is centered on a wavelength of about 500 nm.

8. The method of claim 1 or claim 2 wherein the said second wavelength region is centered on a wavelength of about 550 nm.

9. The method of claim 1 or claim 2 wherein said first image and said second image are formed by a video camera.

10. The method of claim 1 or claim 2 wherein the ratio between each corresponding pair of pixels of said first image and said second image are calculated by a computer implemented algorithm.

11. The method of claim 2 wherein the ratio between said soil reflectance in said first wavelength region and in said second wavelength region is calculated by a computer implemented algorithm.

12. The method of claim 1 or claim 2 wherein said third image data is electronically recorded.

13. The method of claim 1 wherein the bandpass of at least one of said bandpass filters is about 10 nm full width at half maximum.

14. The method of claim 1 wherein the bandpass of both of said bandpass filters are about 10 nm full width at half maximum.

* * * * *